United States Patent
Prasad

(10) Patent No.: US 11,607,398 B2
(45) Date of Patent: *Mar. 21, 2023

(54) CHLOROGENIC ACID COMPOSITION AND METHOD OF WEIGHT MANAGEMENT

(71) Applicant: Vidya Herbs, Inc., Fullerton, CA (US)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 544 days.

This patent is subject to a terminal disclaimer.

(21) Appl. No.: 16/416,709

(22) Filed: May 20, 2019

(65) Prior Publication Data

US 2020/0138765 A1    May 7, 2020

Related U.S. Application Data

(63) Continuation of application No. 14/684,441, filed on Apr. 13, 2015, now abandoned.

(51) Int. Cl.
*A61K 31/216*  (2006.01)
*A61K 36/28*  (2006.01)
*A61K 31/7032*  (2006.01)

(52) U.S. Cl.
CPC ........ *A61K 31/216* (2013.01); *A61K 31/7032* (2013.01); *A61K 36/28* (2013.01)

(58) Field of Classification Search
CPC ... A61K 31/216; A61K 31/7032; A61K 36/28
See application file for complete search history.

(56) References Cited

U.S. PATENT DOCUMENTS

| | | | |
|---|---|---|---|
| 10,039,303 B2 * | 8/2018 | Takeuchi | A61K 36/28 |
| 10,952,985 B2 * | 3/2021 | Prasad | A61P 3/10 |
| 2011/0223281 A1 * | 9/2011 | Ibarra | A61K 45/06 |
| | | | 426/2 |
| 2015/0335673 A1 * | 11/2015 | Yamada | A61P 9/10 |
| | | | 514/27 |

FOREIGN PATENT DOCUMENTS

| | | | | |
|---|---|---|---|---|
| JP | 2008189681 A | * | 8/2008 | |
| WO | WO-2014104157 A1 | * | 7/2014 | A61P 39/06 |
| WO | WO-2015050023 A1 | * | 4/2015 | A23L 1/3002 |

OTHER PUBLICATIONS

Google_scholar_search_10-3-2021_chlorogenic_acid_coffee_beans_lipase (Year: 2021).*
Y. Narita, K. Iwai, T.F Ukunaga, O. NAKAGI. "Inhibitory Activity of Chlorogenic Acid in Decaffeinated Green Coffee Beans against Porcine Pancreas Lipase and Effect of a Decaffeinated Green Coffee Bean Extract on an Emulsion of Olive Oil," Biosci. Biotechnol. Biochem. 76 (15), 2329-2331, 2012. (Year: 2012).*
G. M. Weisz, D. R. Kammerer, R. Carle. Identification and quantification of phenolic compounds from sunflower (*Helianthus annuus* L.) kernels and shells by HPLC-DAD/ESI-MSn. Food Chemistry 115 (2009) 758-765. (Year: 2009).*
Machine translation of JP-2008189681-A from EPO. (Year: 2022).*

* cited by examiner

*Primary Examiner* — Michael P Cohen
(74) *Attorney, Agent, or Firm* — TMB Law; Timothy M. Brown

(57) ABSTRACT

A composition formulated from sunflower, including *Helianthus annulus* and methods for use of the composition for treating obesity in a subject.

11 Claims, 8 Drawing Sheets

CHLOROGENIC ACID COMPOSITION AND METHOD OF WEIGHT MANAGEMENT

CROSS REFERENCE TO RELATED APPLICATIONS

This application is a continuation of application No. 14/684,441, filed Apr. 13, 2015, the entire contents of which are in incorporated herein by reference for all purposes.

FIELD OF THE INVENTION

The invention generally relates to a composition formulated from sunflower and methods for the use of the composition in the treatment of obesity and obesity management.

BACKGROUND

Sunflowers are botanically classified as in the genus *Helianthus* belonging to family compositae. They are a large plant and are grown throughout the world because of their relatively short growing season. Domesticated sunflowers typically have a single stalk topped by a large flower. This is significantly different from the smaller, multiply branched wild sunflower. During the growing season, the individual flowers are each pollinated. The sunflower plants reach various heights, but most are from 1.52-2.1 meters tall. Seed development begins moving from the outer rim of the flower toward the center. It generally takes 30 days after the last flower is pollinated for the plant to mature (Agribusiness Handbook, 2010).

Sunflowers, which are used mainly as an ornamental crop, have in recent times become an important source of an edible and nutritious oil. There are two types of sunflower one being an oilseed type and the other a confectionery type. The latter accounts for only 10% of the total sunflower production. The dehulled seeds (kernels) are sold as confectionary nuts. Sunflowers apart from being a source of oil, are also a source of lecithin, tocopherols, furfural and nutritious meal used mainly as bird and animal feed. The seed itself is edible and its oil is used throughout the world for frying and cooking. It is also used as poultry feed. The seed has been used by Native Americans for more than 5,000 years and was introduced in Europe by the Spanish conquerors (Nagaraj, 1995).

The sunflower seed is pointed at its base, and round at the top. The outer pericarp (hull) is dark colored. Beneath the hull there is a papery white testa. The kernel inside consists of two cotyledons attached to a protruding radicle and embryo. The kernel constitutes 60-70% of the seed weight. The seed size varies from 6 to 25 mm in length, 3 to 15 mm in width and 3 to 8 mm in thickness. The 1,000 seed weight ranges from 40 to 60 g in the case of oilseed type and up to 100 g in the case of the confectionery type. The oil content of the kernel ranges from 48-53% while it is from 28-35% for the whole seed. The protein content of the seed is 14-19%. The crude fiber varies between 16-27% with an ash percentage of 2-3 (Nagaraj, 1995).

The principal phenolic constituents of sunflower seeds are chlorogenic acid (CGA), smaller quantities of caffeic acid (CA), cinnamic, coumaric, ferulic, sinapic and hydroxycinnamic and finally traces of vanillic, syringic and hydroxy-benzoic acids. CGA represent 700 g/kg of the total acids and are mainly located in the kernel (part of seed). The presence of CGA in sunflower is particularly important because of its association with the dark green and brown colors developed under alkaline conditions or during aqueous processing (Pedrosa et al., 2000).

Sunflower seed is an excellent source of vitamin E, which is the body's primary soluble anti-oxidant. Sunflower seeds have significant anti-inflammatory activity. It has been found that sunflower is a good source of magnesium which helps to reduce the severity of migraine headaches, as well as risk of heart attack and stroke. Sunflower seed has betaine which exhibits cardiovascular benefits. Sunflower seeds have skin care and skin protection properties. Sunflower seeds possess analgesic activities (Preedy et al., 2011).

Obesity is defined in terms of body mass index (BMI), which is calculated as body weight divided by square of height, and it is mainly a result of an imbalance between energy intake and expenditure. The World Health Organization (WHO) has reported that worldwide obesity has more than doubled since 1980. In 2008, more than 1.4 billion adults worldwide aged 20 or older were overweight, with women outnumbering men by 3:2. More than 40 million children under the age of five were overweight in 2010 and in 2012 obesity represented the fifth leading risk for global deaths, with at least 2.8 million adult deaths. Many diseases such as hypertension, non-insulin dependent hyperlipidemia, and diabetes mellitus and coronary heart diseases are attributable to being overweight or obese.

One of the approaches to reduce obesity is treatment with synthetic drugs such as sibutramine, rimonabant, phentermine, diethylpropion, zonisamide, topiramate and orlistat. Sibutramine and rimonabant were recently withdrawn from the market due to adverse side effects. For example, Sibutramine could lead to an increased risk of heart attack and stroke in high risk cardiac patients, whereas the latter could lead to potentially serious psychiatric disorders (Ghazali et al., 2013).

Hence, there is an urgent need for safer and more efficient anti-obesity agents derived from natural sources that are less damaging than synthetic anti-obesity treatments.

SUMMARY OF THE INVENTION

It is an object of the invention to provide a composition formulated from *Helianthus annuus* seed for managing obesity, wherein the composition comprises by weight, about 47.50±2.5 w/w % total polyphenols content.

It is a further object of the invention to provide a composition for managing obesity, wherein the composition comprises by weight, about 42.50±2.5 w/w % chlorogenic acid.

In some aspects of the invention, the composition is non-toxic as determined by the Ames test for mutagenicity.

In some aspects of the invention, the composition has anti-oxidant activity, including, but not limited to DPPH scavenging activity, superoxide anion scavenging activity, reducing power activity, total anti-oxidant activity, and protection against oxidative DNA damage.

In some aspects of the invention, the composition inhibits pancreatic lipase.

In some aspects of the invention, the composition has anti-lipase activity.

It is an object of the invention to provide a composition for treating obesity comprising 42.50±2.5% w/w chlorogenic acid.

In some aspect, the composition comprises at least one of 3CQA, 5CQA, 4 CQA, and Di CQA.

In some aspects, the composition comprises, by weight, a chlorogenic isomer selected from the group consisting of about 4.1±1.42% 3CQA, about 28±4.65% 5CQA, about 6.5±2.25 4 CQA, about 0.84±0.26 4CQA, about 0.84±0.26 3,4 Di CQA, about 1.23±0.34 3,5 Di CQA, and about 1.85±0.42 4,5 Di CQA.

In some aspects, the composition comprises (i) about 4.1±1.42% 3CQA, (ii) about 28±4.65% 5CQA, (iii) about 6.5±2.25 4 CQA, or about 0.84±0.26 4 CQA, and (iv) about 0.84±0.26 3,4 Di CQA, about 1.23±0.34 3,5 Di CQA, or about 1.85±0.42 4,5 Di CQA.

In some aspects, the composition is formulated from *Helianthus annuus*.

In some aspects, the composition has an antioxidant scavenging activity of about 87.88% at a concentration of about 100 μg/ml as determined by DPPH assay.

In some aspects, the composition has a superoxide scavenging activity of about 80.41% at concentration of about 100 μg/ml.

In some aspects, the composition has a total antioxidant activity of about 80.41% at concentration of about 18.59 equivalents of ascorbic acid.

In some aspects, the composition has DNA scission protective effect of about 91.82% at a concentration of about 100 μg/ml.

In some aspects, the composition inhibits lipase activity by at least 40% at a concentration of about 100 μg/ml.

DEFINITIONS

Figure 1:
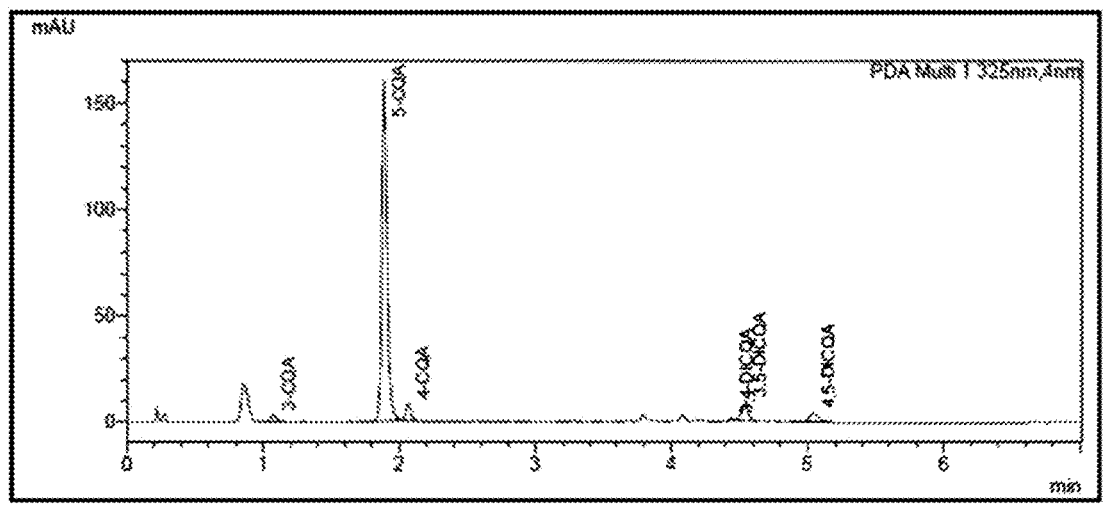
FIG. 1 shows an HPLC chromatogram analysis for a composition according to the invention.
Figure 2:
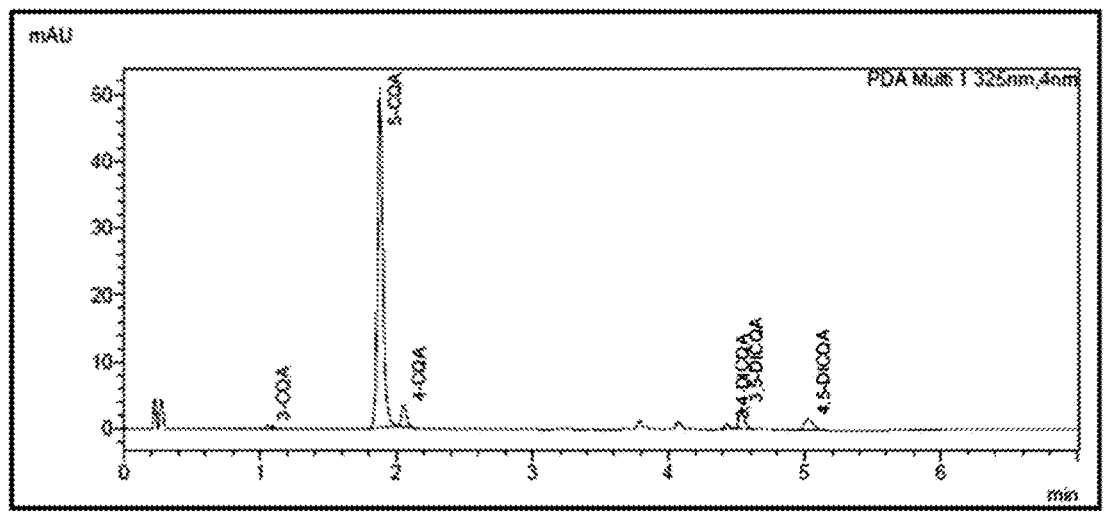
FIG. 2 shows an HPLC chromatogram analysis for a composition according to the invention.

As used herein, the phrase "sunflower material" refers to any portion of a sunflower plant belonging to the genus *Helianthus*, including, but not limited to seeds, leaves, stems, fruit, stalks, flowers, pollen, roots, or a combination thereof. Sunflower material may be obtained from *Helianthus annuus*.

The phrase "body mass index" as used herein refers to a ratio of height to body weight that is calculated as follows:

$$BMI = \frac{mass_{kg}}{height_m^2} = \frac{mass_{lb}}{height_{in}^2} \times 703$$

The terms "obese" and "obesity" as used herein refer to a subject having a body mass index of 30 or higher.

The term "overweight" as used herein refers to a subject having a body mass index of 25 to 29.9.

The term "healthy weight" as used herein refers to a subject having a body mass index of 18.5 to 24.9.

The term "underweight" as used herein refers to a subject having a body mass index of below 18.5.

The term "reduce" as used herein refers to any measurable decrease in a parameter relative to control conditions.

The phrase "treating obesity" as used herein refers to reducing BMI in an obese subject, reducing body fat in an obese subject, or reducing body weight in a subject.

The term "about" as used herein refers to a value that is 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Detailed Specification

The invention generally relates to a composition derived from sunflower (e.g. *Helianthus annuus*) and methods for the use of the composition in the treatment of obesity.

The composition may be derived from any sunflower material capable of providing the composition described herein. The composition may be derived from seeds, leaves, stems, fruit, stalks, flowers, pollen, roots, or a combination thereof. In some aspects, the composition is derived from sunflower seeds. The composition may be derived from derived from sunflower material from *Helianthus annuus*.

An aspect of the invention relates to the formulation of the composition. The composition may be formulated to attain about 20-60% w/w polyphenols. The composition may have a total polyphenol content, by w/w, of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, as well as any amount intervening these specifically described amounts. In one non-limiting embodiment, the composition has a total polyphenol content of 47.50±2.5 w/w %. The composition may have a total polyphenol content of 42.50±2.5 w/w %.

The composition may be formulated to attain a particular chlorogenic acid content. The composition may have a total chlorogenic acid content of between about 20-60% w/w. The composition may have a total chlorogenic acid content, by weight, of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, as well as any amount intervening these specifically described amounts. The total chlorogenic acid content may be 42.50±2.5 w/w %. The total chlorogenic acid content may be constituted from one or more of 3 CQA, 5 CQA, 4 CQA, 3,4 Di CQA, 3,5 Di CQA, 4,5 Di CQA. The total chlorogenic acid content may contain, for example, a chlorogenic acid content of about 1-15% w/w 3 CQA, about 5-50% w/w 5 CQA, about 1-20% w/w 4 CQA, about 0.5-10% w/w 3,4 Di CQA, about 0.5-10% w/w 3,5 Di CQA, about 0.5-10% w/w 4,5 Di CQA, or combination thereof. The composition may contain 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA.

The composition may be formulated to achieve one or more of the effects described herein. Such effects include, but are not limited to, reducing BMI in a subject, reducing body fat in a subject, and/or inhibiting lipase activity in a subject. Once skilled in the art will appreciate that methods for measuring the inhibition of lipase are known in the art and include, for example, in vitro lipase enzyme assays.

The composition of the invention may be formulated to contain one or more chlorogenic acids. Such chlorogenic acids include, but are not limited to, 3-O-Caffeoylquinic acid (3 CQA), 4-O-Caffeoylquinic acid (4 CQA), 5-O-Caffeoylquinic acid (5 CQA), 5-O-Feruloylquinic acid, 3,4-O-Dicaffeoylquinic acid (3,4 Di CQA), 3,5-O-Dicaffeoylquinic acid (3, 5 Di CQA), 4,5-O-Dicaffeoylquinic acid (4,5 Di CQA), and combinations thereof.

The composition of the invention finds use in treating or managing obesity in a subject. The composition may be administered to an obese subject in an amount effective to reduce body fat in the subject. The composition may be administered to an obese subject to reduce body mass index (BMI) in the subject. The subject may be a mammalian subject, including humans, cattle, horses, sheep, pigs, poultry, dogs, or cats. In a preferred embodiment, the subject is human.

The composition may be administered to reduce the BMI in a subject. The composition may be administered to reduce BMI in an obese subject. The composition may be administered to reduce BMI in an overweight subject. The composition may be administered to reduce BMI in a healthy weight subject. It is also contemplated that the composition may be administered to reduce BMI in an underweight subject. The composition may be administered to reduce body fat in an obese subject. The composition may be administered to reduce body fat in an overweight subject. The composition may be administered to reduce body fat in a healthy weight subject. The composition may be administered to reduce body fat in an underweight subject.

In some aspects, the composition is administered to maintain the BMI or body fat level in a subject. That is, the composition is administered to keep the BMI or body fat of the subject at their current BMI or body fat level. The composition may be administered to maintain the BMI or body fat level in an obese subject. The composition may be administered to maintain BMI or body fat level in an overweight subject. The composition may be administered to maintain BMI or body fat level in a healthy weight subject. The composition may be administered to maintain BMI or body fat level in an underweight subject.

In some aspects of the invention, the composition is administered to prevent an increase in BMI or body fat in a subject. The composition may be administered to prevent an increase in BMI or body fat in an obese subject. The compositions may be administered to prevent an increase in BMI or body fat in an overweight subject. The composition may be administered to prevent an increase in BMI or body fat in a healthy weight subject. The composition may be administered to prevent an increase in BMI or body fat in an underweight subject.

Without being limited to any particular theory or mechanism, the composition of the invention imparts its effects by inhibition of lipase in a subject. Lipases (e.g. triacylglycerol hydrolase E.C. 3.1.1.3) are enzymes that catalyze the hydrolysis of ester bonds of triacylglycerols (fats and oils) to produce free fatty acids such as diacylglycerols, monoglycerols and glycerol. In the small intestine of mammals, the digestion of dietary triacylglycerols (TAG) is essentially due to the action of pancreatic lipase. The end products after they have been absorbed by the body are responsible for the development of obesity. Therefore, if the hydrolysis of TAG, and thus, its movement from the intestinal lumen into the body is stopped or minimized, the prevalence of obesity can be reduced. The composition may inhibit pancreatic lipase (HPL), pancreatic lipase related protein 2 (PLRP2), hepatic lipase (HL), endothelial lipase, and lipoprotein lipase. In one non-limiting embodiment, the composition inhibits pancreatic lipase.

One aspect of the invention concerns the dosage of the composition. The composition may be administered at a dose of between about 5 mg/day to about 500 mg/day. The composition may be administered at a dose between about 20 mg/day to about 1 mg/day. The composition of the invention may be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition may be administered at a dosage of between about 400 mg/day to about 500 mg/day, between about 300 mg/day to about 400 mg/day, between about 200 mg/day to about 300 mg/day, between about 100 mg/day to about 200 mg/day, between about 100 mg/day to about 200 mg/day, or about 20 mg/day to about 100 mg/day. It is contemplated that the composition may be administered at any dosage that intervenes the dosages called out in this specification.

The composition may be administered to the subject topically, orally, buccally, sub-lingually, parenterally, intravenously, intravaginally, rectally, or by inhalation. The composition may be administered as a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, or injection. The composition may be formulated for oral administration. The composition may formulated with flavorings, minerals, vitamins, or a combination thereof.

The composition finds use in a variety of therapeutic and preventive applications. In some embodiments, the composition is administered to a subject for preventing oxidation and the production of free radicals in the subject (i.e. antioxidant activity). Thus, the composition may have a nutritive effect for maintaining and promoting health in a subject.

The present disclosure is further described in the light of the following non-limiting examples which are set forth for illustration purpose only and not to be construed for limiting the scope of the disclosure.

Example 1—Preparation of Sunflower Material 100 kg of sunflower seed powder was taken into a cleaned vertical 1.0 KL extractor. The bottom of the extractor comprises of a perforated plate on which filtration cloth was fixed. The bottom of the extractor was connected to a transfer pump input and output of the transfer pump was connected to T bend. One end was connected to extractor top for circulation of extraction mass while extraction period and other end of T bend were connected to receiver tank.

The above mentioned mass was extracted with 7-8 bed volumes of demineralized water. Extraction was continued at 80-85° C. temperature about 7-8 hrs with continuous circulation of extract with transfer pump. After completion of extraction, filter the extract through 5 micron SS candle filter and collect clear extract in a receiver tank. The bed was re-extracted by adding 5-6 bed volumes of demineralized water 3 more times at 80-85° C. temperature about 7-8 hrs and filter through 5 micron SS candle filter. Collect all the extracts in a receiver tank and combined extract was concentrated in a reactor under vacuum at 80-85° C. till extract moss TDS reaches to 25-30 w/v % and cool to room temperature. Separate oily layer and collect the aqueous layer.

The above aqueous layer was taken and the solution was adjusted to pH to 2-2.2 with dilute sulphuric acid and stirred well about 15 minutes. The solution was filtered through celite bed to make it into clear solution. The solution was loaded into a macroporus XAD-16N (Made by Rohm & Haas Company) resin column at the rate of 2-3 bed volumes/hour. The resin bed was washed with 4-6 bed volumes of demineralized water at the rate of 2-3 bed volumes/hour. Further it was eluted with 3-4 bed volumes of 70-75 v/v % ethyl alcohol at the rate of 2-3 bed volumes/hour. The eluent was concentrated in a reactor at 75-80° C. till free from ethyl alcohol. The extract mass was dissolved into demineralized water till the TDS reaches to 25-30 w/v %. Spray dries the extract at 185-190° C. Yield of the extract about 2.8±0.2 w/w %.

Example 2—Spectrophotometric and HPLC Derivation

The material obtained under Example 1 was subjected to phyto-chemical derivation through spectrophotometric and HPLC estimations.

A. Derivation of Polyphenol Content by Folin-Ciocalteous Method

Standard Preparation:

Dissolve 100 mg of STD (99.9% pure) in 100 ml of volumetric flask by using 50% methanol solution (1000 ppm Chlorogenic acid stock standard). From this 1000 ppm stock standard prepare 30 ppm, 60 ppm, 90 ppm, 120 ppm, 150 ppm and 180 ppm standard solutions by diluting using 50% methanol solution.

Sample Preparation:

15-20 mg of the preparation from Example 1 was placed into 100 ml of volumetric flask, about 50 ml of 50% methanol solution was added and the mixture sonicated for 5 mins, then diluted to 100 ml with 50% methanol, then further diluted to 5.0 ml of above solution to 10 ml using 50% methanol.

Prepared a series of test tubes (one for blank, each STDs and samples) each containing 15 ml of 50% methanol solution+1 ml of Folin-Ciocalteus reagent followed by 1.0 ml of standard, sample or 50% methanol solution. Allowed the above solutions at room temperature for 10 mins. Added 3.0 ml of 20% $Na_2CO_3$ solution to each tube, mixed well. Placed tubes in a water bath at 40° C. for 20 minutes. Immediately placed tubes into an ice bath upon removal from water bath for 2 minutes. Removed the tubes and allowed to come to room temperature. Measured the absorbance of blank, standards and samples at 755 nm. (Table 1)

Calculation $$\% \text{ Total Polyphenols} = \frac{\frac{A\ sample - b}{m} \times V \times DF \times 100}{W_{sample} \times 1000}$$

Where,

V—Original volume 50 ml $W_{sample}$—sample weight in grams

DF—dilution factor $A_{sample}$—sample absorbance m, b—Coefficients of standard curve Slope and y-intercept.

TABLE 1

ESTIMATION OF TOTAL POLYPHENOLS

| S. N. | Phyto-constituents | Analysis Method | Sunflower seed (Raw material) (%) | Composition |
|---|---|---|---|---|
| 1 | Total polyphenols | Spectrophotometric | 1.80 ± 0.40 w/w %. | 47.50 ± 2.5 w/w % |

Result

Percentage of total polyphenols in the composition (47.50±2.5 w/w %) was higher as compared to raw material of sunflower seed extract (1.80±0.40 w/w %).

B. Derivation of Chlorogenic Acid Content by HPCL

Analytical Parameters:

Column: XB-C18 100A, 2.6 µm, 50× 2.1 mm Phenomenex. (Kinetex)
Pump: Nexera X2, LC-30AD Shimadzu
Detector: SPD-M20A PDA
Wave length: 325 nm
Flow rate: 0.6 mL/min
Volume of injection: 1 µL
Run time: 7 min.
Mobile phase: 0. 1% Formic acid in HPLC grade water: Acetonitrile
Reference standard: Chlorogenic acid—98%
Gradient:

| Time | B concentration (Acetonitrile) |
|---|---|
| 0.01 | 5 |
| 4.0 | 20 |
| 5.0 | 5 |
| 7.0 | Stop |

Standard Preparation:

15-20 mg of standard chlorogenic acid (98%) was weighed into a 50 ml standard flask, add 30 ml 70% methanol and sonicated about 10 minutes. Make up to the mark with same solvent. Pipetted out 10 mL of the above solution to 50 ml standard flask and make up to the mark with same solvent and sonicated about 10 minutes.

Sample Preparation:

40-50 mg of sample was weighed into 50 ml standard flask, added 30 ml 70% methanol and sonicated about 10 minutes. Make up to the mark with same solvent. Pipetted out 10 mL of the above solution to 50 ml standard flask and make up to the mark with same solvent and sonicated about 10 minutes.

Composition Sample Preparation:

1000-1500 mg of composition was weighed into 100 ml RB flask, added 40 ml 70% methanol. Refluxed about half an hour and cooled. Filtered in a 100 ml standard flask. Repeated extraction 2 more times with 30 ml of 70% methanol and filter. Make up the volume to 100 ml using 70% methanol and sonicated about 10 minutes.

Calculation:

$$\% \text{ of chlorogenic acids} = \frac{\text{Peak area of the sample} \times \text{Conc. of the } STD \times \text{purity of the } STD}{\text{Peak area of the standard} \times \text{Conc. of the sample}}$$

TABLE 2

PERCENTAGE OF TOTAL CHLOROGENIC ACID

| S. N. | Phyto-constituents | Analysis Method | Sunflower seed (Raw material) (%) | Composition (%) |
|---|---|---|---|---|
| 1 | Chlorogenic acids | HPLC | 1.65 ± 0.25 w/w %. | 42.50 ± 2.5 w/w % |

TABLE 3

CHLOROGENIC ACID ISOMERS

| S. N. | Chlorogenic acid isomers | Sunflower seed (%) | Composition (%) |
|---|---|---|---|
| 1 | 3 CQA | 0.04 ± 0.02 w/w % | 4.1 ± 1.42 w/w % |
| 2 | 5 CQA | 1.35 ± 0.25 w/w % | 28 ± 4.65 w/w % |
| 3 | 4 CQA | 0.08 ± 0.04 w/w % | 6.5 ± 2.25 w/w % |
| 4 | 3,4 Di CQA | 0.0068 ± 0.0001 w/w % | 0.84 ± 0.26 w/w % |
| 5 | 3,5 Di CQA | 0.1 ± 0.04 w/w % | 1.23 ± 0.34 w/w % |
| 6 | 4,5 Di CQA | 0.08 ± 0.02 w/w % | 1.85 ± 0.42 w/w % |

Result

Percentage of total chlorogenic acid in the composition from Example 1 (42.50±2.5 w/w %) was higher as compared to raw material of sunflower seed extract (1.65±0.25 w/w %).(Table 2,3)

C. Chlorogenic Acid Finger Print of Composition by LCMS/MS

Analytical Parameters:

Column: XB-C18 Phenomenex (Kinetex), 100 A, 2.6 µm & 50×2.1 mm
Pump: Nexera X2, LC-30AD Shimadzu
Detector: SPD-M20A PDA and LCMS/MS 8040
Wavelength: 325 nm
Flow rate: 0.6 mL/min
Volume of injection: 1 µL
Run time: 7 min.
Mobile phase (A: B): Acetonitrile: 0. 1% Formic acid in LCMS grade water
DL Temp.: 4000 C
Nebulizing gas flow: 3 L/min.
Heat block temp: 5000 C
Drying gas flow: 15 L/min.
MS detection: ESI-ve mode, SIM at m/z 353 and 515, MRM at m/z 191,178 and 353
Gradient:

| Time | B concentration (Acetonitrile) |
|---|---|
| 0.01 | 5 |
| 4.0 | 20 |
| 5.0 | 5 |
| 7.0 | Stop |

Sample Preparation:

40-50 mg of sample was weighed into 50 ml standard flask, 30 ml 70% methanol (LCMS) was added and sonicated about 10 minutes. Make up to the mark with same solvent. Pipetted out 10 mL of the above solution to 50 ml standard flask and make up to the mark with same solvent and sonicated about 10 minutes.

Raw Material Sample Preparation:

1000-1500 mg of raw material powder was weighted into 100 ml RB flask, add 40 ml 70% methanol (LCMS). Reflux about half an hour and cool. Filter it in a 100 ml standard flask. Repeat extraction 2 more times with 30 ml of 70% methanol and filter. Make up the volume to 100 ml using 70% methanol and sonicated about 10 minutes.

Result

Figure 3:
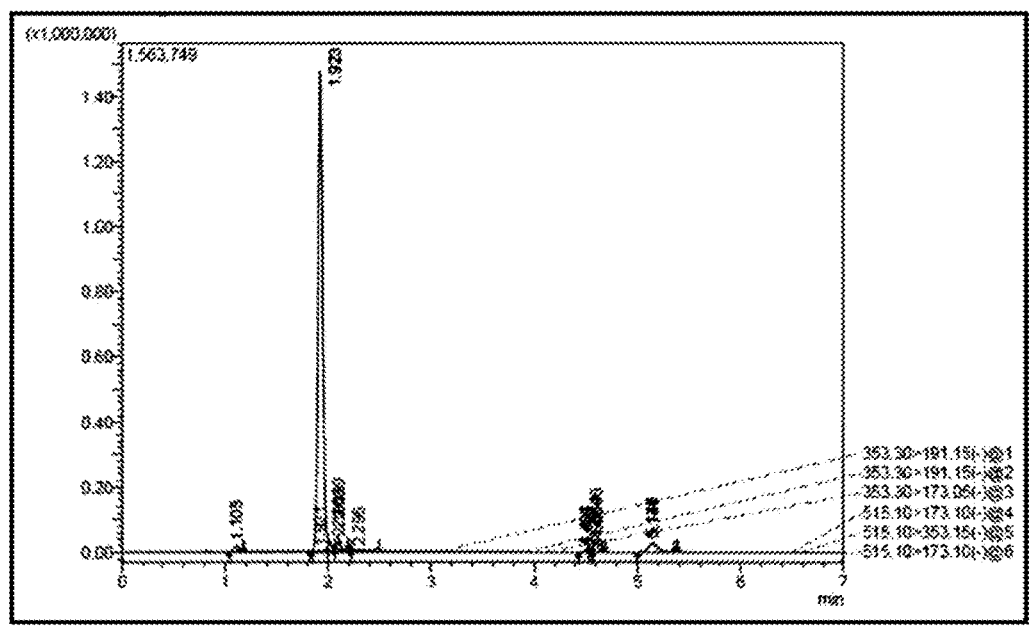
FIG. 3 shows an LCMS/MS chromatogram for a composition according to the invention.
Figure 4:
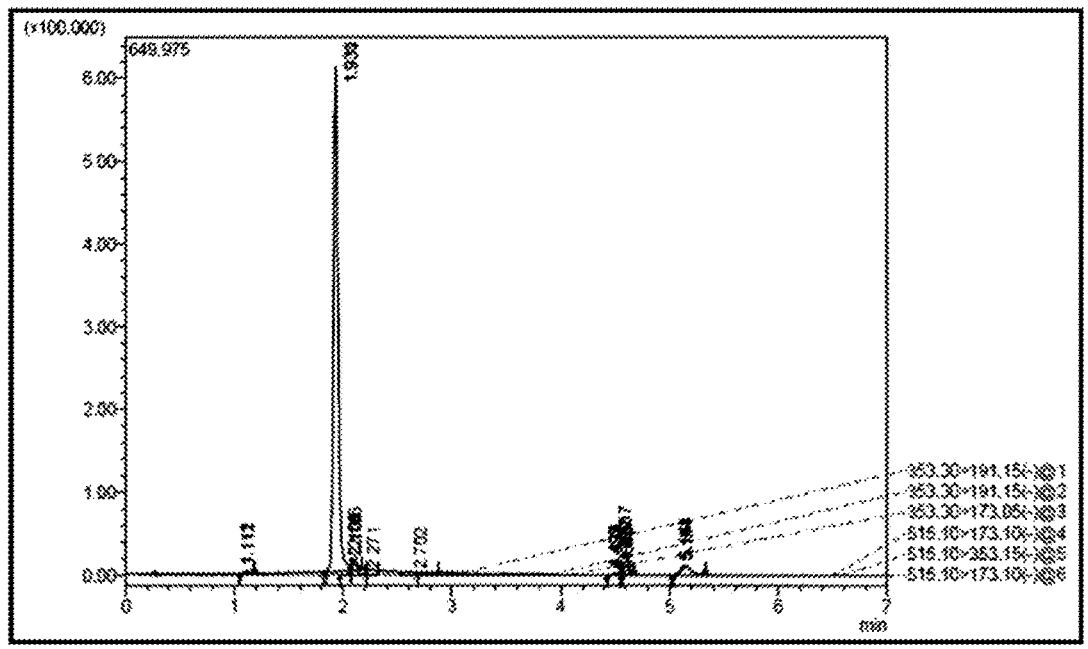
FIG. 4 shows an LCMS/MS chromatogram for a composition according to the invention.

The fingerprint of sunflower seed (raw material) and the composition from Example 1 was established by the LC-MS/MS method. (FIG. 3 and FIG. 4)

Example 3—Toxicity Study

The Ames test is widely used in the determination of possible gene mutations by various agents. A positive response in any single bacterial strain either with or without metabolic activation is sufficient to designate a substance as an antimutagen. It is estimated that 90% of all carcinogens also are mutagens, and with this figure in mind, Bruce Ames and his colleagues developed a test in the 1970s that uses special bacteria that are very sensitive to mutagenic agents. The Food and Drug Administration (FDA) now uses the Ames test to screen many chemicals rapidly and inexpensively. Those few chemicals that appear to be mutagenic by the Ames test are tested further in animals to assess their ability to cause cancer.

The *Salmonella* mutagenicity test was specifically designed to detect chemically induced mutagenesis both in presence and absence of metabolic activation. This assay helps to identify substances that can produce genetic damage that leads to gene mutations. Mutant strains of *Salmonella typhimurium* that are used in AMES assay cannot synthesize histidine, and are very susceptible to additional mutations because they lack the normal repair mechanisms found in bacteria. These mutant strains are more permeable than wild-type bacteria to external chemicals, including potential mutagens. In order for these cells to survive on a plate that lacks histidine, they must regain the ability to synthesize histidine by undergoing another mutation that corrects the original mutation that prevented the production of the missing enzyme. This type of mutation is known as a back mutation, or reversion, because this second mutation returns the mutant to the wild-type (prototrophic) phenotype. This reversion can happen spontaneously due to incorrect DNA replication or as the result of a mutagen.

In this assay specific strains of the bacteria *Salmonella typhimurium* (TA 98, TA 100) will be used to detect mutations. These strains of *S. typhimurium* used are known as auxotrophs and will not grow unless the nutrient is supplied in growth media. In order for these cells to survive on a plate that lacks histidine, they must regain the ability to synthesize histidine by undergoing another mutation that corrects the original mutation that prevented the production of the missing enzyme. The number of colonies that revert and grow (in presence and absence of metabolic activating system) is proportional to the mutagenicity of the test compound.

Procedure

Animal Treatment

The *S. typhimurium* strains used in the experiments were: TA 100 and TA98. Liver cytosolic fractions were prepared from young adult male Wistar rats. According to INVITTOX Protocol (Borenfreund and Puemer, 1990), animals were sacrificed after 5 days of receiving daily i.p. injections of sodium Phenobarbital at 30 mg/kg (day 1) and 60 mg/kg (days 2-5). On the third day, 80 mg/kg of 5, 6 b-naphtoflavone were also administrated. The 9000 g liver supernatant (S9) was split into 1 mL aliquots, frozen and stored at −80° C.

Assay

The standard preincubation method in the presence and absence of S9 was performed according Maron and Ames, 1983. For this study, the composition of Example 1 was prepared in DMSO at stock concentration of 10 mg/mL and it was added to the cultures at 1, 2 & 3 mg/plate. Negative (vehicle-DMSO) and positive controls 4-Nitro-Phenylene diamine and EtBr were included.

Briefly, 0.5 ml of S9 mix (or 0.1 M phosphate buffer, pH 7.4), 0.1 ml of bacterial culture and 0.1 ml of test solution (or solvent) were added to each tube. The mixture was vortexed, and then allowed to incubate at 37° C. with shaking for 30 min. Following this preincubation period, 2.0 ml of molten top agar (45° C.) supplemented with histidine and biotin (0.5 mM) was dispensed into the tubes, which were immediately vortexed and the contents poured onto the surface of bottom minimal glucose agar Vogel and Bonner, 1956. Then the agar overlay had solidified, the plates were inverted and placed in a 37° C. incubator. After incubation for approximately 48 h the revertant colonies were counted.

Results

Figure 5:
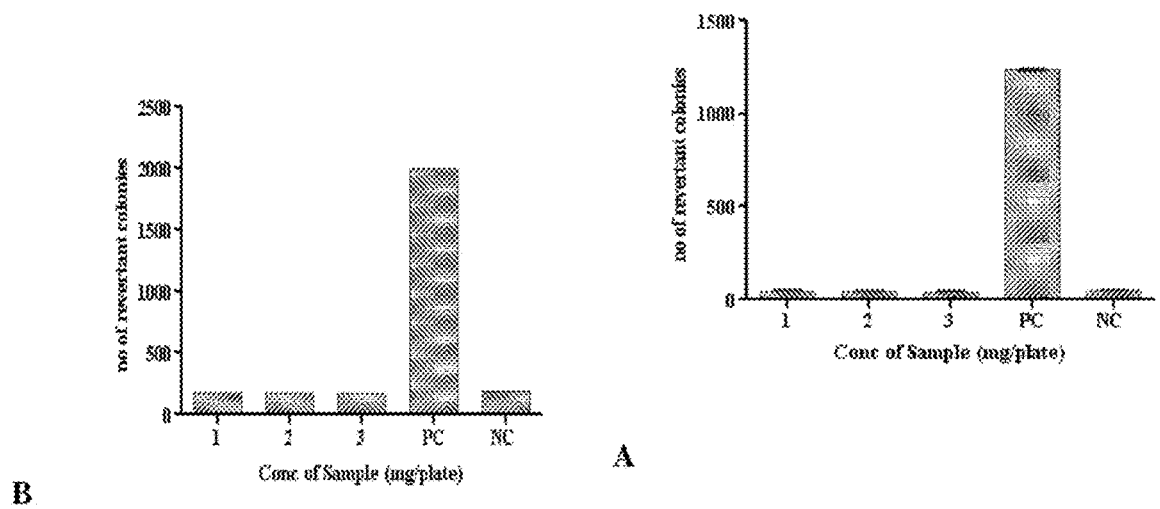
FIG. 5 shows mutagenic activity of a composition of the invention against (A) TA 100 and (B) TA98 in the absence of S9 fraction.
Figure 6:
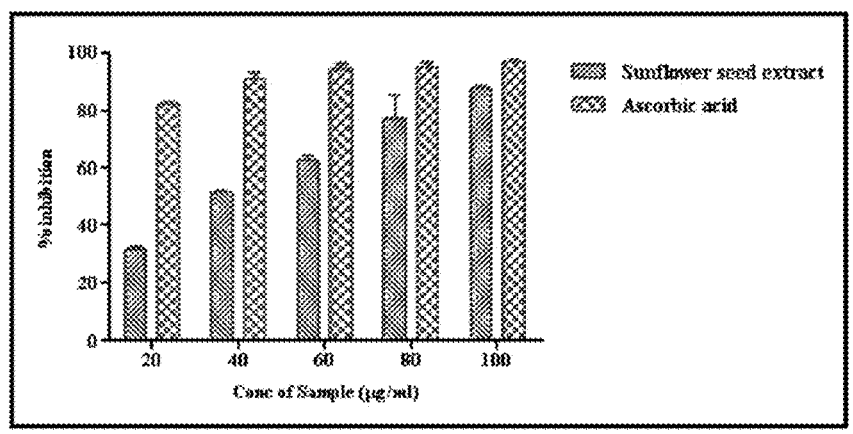
FIG. 6 shows inhibition of DPPH radical activity by a composition according to the invention.

From the above results, the strains of *S. typhimurium* viz., TA98 & TA100 exposed to different concentrations of the composition did not show a twofold or greater increase in the mean number of revertants as compared to the negative control group as given in Table 4. All strains used in the study exhibited a marked increase (>10-fold) in the number of revertants when treated with positive control agents. The results confirmed the sensitivity of the test strains to mutagens and thus the validity of the assay. The results indicated that the mean number of histidine revertants in the treatment groups were comparable to the mean number of revertants in the negative control group in the *S. typhimurium* tester strains viz., TA98 & TA100 both in the absence and the presence of metabolic activation. The composition up to 5 mg/plate in the presence and absence of metabolic activation was found to be non-mutagenic to *S. typhimurium* tester strains. (Table 4, FIG. 5, FIG. 6).

TABLE 4

MUTAGENIC ACTIVITY

Revertant colonies/plate (Mean n = 2 ± S.D.)

| Concentration | TA 100 | | TA 98 | |
|---|---|---|---|---|
| (mg/plate) | −s9 | +s9 | −s9 | +s9 |
| NC (DMSO) | 181.0 ± 5.65 | 184 ± 2.8 | 41.5 ± 2.12 | 49.0 ± 1.4 |
| 2 | 179.5 ± 0.7 | 180.5 ± 4.9 | 39.5 ± 0.7 | 45.5 ± 2.1 |
| 4 | 170.5 ± 2.1 | 179.0 ± 5.6 | 40.5 ± 0.7 | 44.0 ± 7.0 |
| 5 | 167.0 ± 2.8 | 182 ± 2.8 | 41.0 ± 1.4 | 39.0 ± 2.8 |
| PC SA | 2345.5 ± 6.3 | NA | NA | NA |
| PC NOP | NA | NA | 610 ± 11.3 | NA |
| PC 2AF | NA | 2737 ± 4.9 | NA | 1560 ± 3.53 |

Key:
S.D. = Standard deviation,
NC = Negative control,
DMSO = Dimethyl sulfoxide,
PC = Positive control,
NOP = 4-Nitro-O-phenylene diamine,
SA = Sodium azide,
2AAF = 2-aminoanthracene,
NA = Not Applicable,
n = No. of replicates Example 4—In-Vitro Anti-Oxidant Activities 4.1. DPPH Radical Scavenging Assay The free radical scavenging capacity of the test sample was determined using DPPH scavenging assay. DPPH solution was prepared in 95% methanol. Freshly prepared DPPH solution was taken in test tubes and different concentration of test samples were added and incubated for 20 min. The absorbance was read at 517 nm using a spectrophotometer. Blank was prepared containing the same volume of reaction mixture without any tested samples. The percentage of scavenging was calculated using the formula:

% Scavenging=$Ac-As/Ac \times 100$

Where $A_C$ was the absorbance of the control (blank) and $A_S$ was the absorbance in the presence of the composition (Braca et al., 2001).

Result

Figure 7:
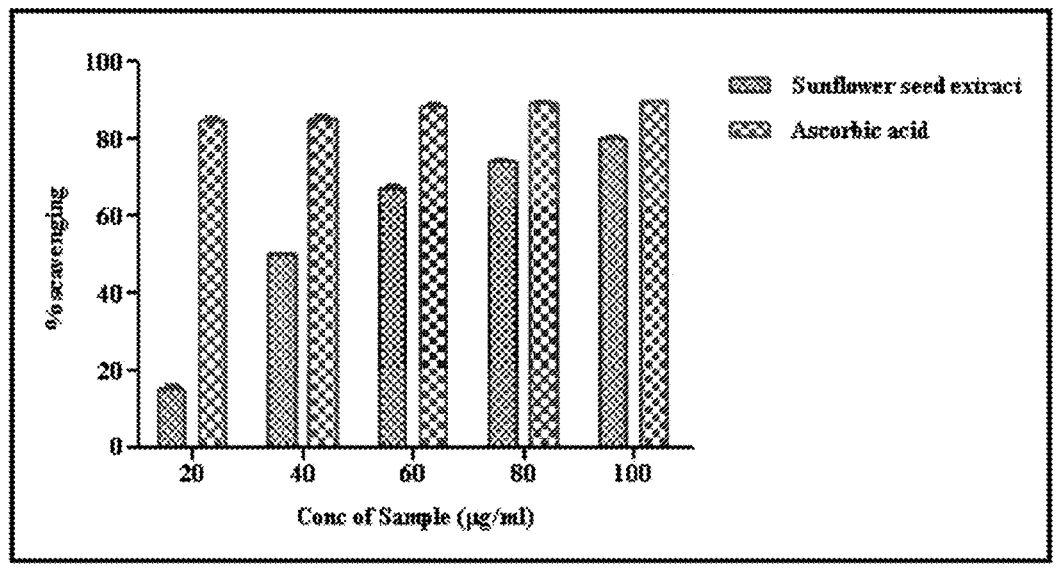
FIG. 7 shows superoxide anion scavenging activity of a composition according to the invention.

Table 5 shows the concentration dependent increase in DPPH radical scavenging activity of the composition, compared with ascorbic acid. It was observed that the composition had maximum activity of 87.88% at concentration of 100 μg/ml, which was comparable with ascorbic acid (96.71%) (Table 5, FIG. 7).

TABLE 5

DPPH SCAVENGING ACTIVITY

| | Composition | | Ascorbic acid | |
|---|---|---|---|---|
| Conc in μg/ml | Absorbance @517 nm | % inhibition | Absorbance @517 nm | % inhibition |
| Blank | 2.281 | | 0.274 | |
| 20 | 1.556 | 31.78 | 0.046 | 83.21 |
| 40 | 1.097 | 51.88 | 0.025 | 90.88 |
| 60 | 0.855 | 62.52 | 0.015 | 94.53 |
| 80 | 0.514 | 77.42 | 0.014 | 94.89 |
| 100 | 0.277 | 87.88 | 0.009 | 96.72 |

4.2. Superoxide Anion Scavenging Activity

Superoxide anion scavenging activity of the composition of Example 1 was measured according to the method of Nishimiki et al., 1972. Prepared all the solutions in this experiment using phosphate buffer (pH 7.4). Added 1 ml of NBT (156 μM), 1 ml of NADH (468 μM) and 3 ml of test samples to all test tubes. The reaction was started by adding 100 ml of PMS (60 μM) and incubated the mixture at 25° C. for 5 min followed by measurement of absorbance at 560 nm. The percentage of scavenging was calculated using formula:

% Scavenging=$Ac-As/Ac \times 100$

Where $A_C$ was the absorbance of the control (blank) and As was the absorbance in the presence of the composition.

Result

Figure 8:
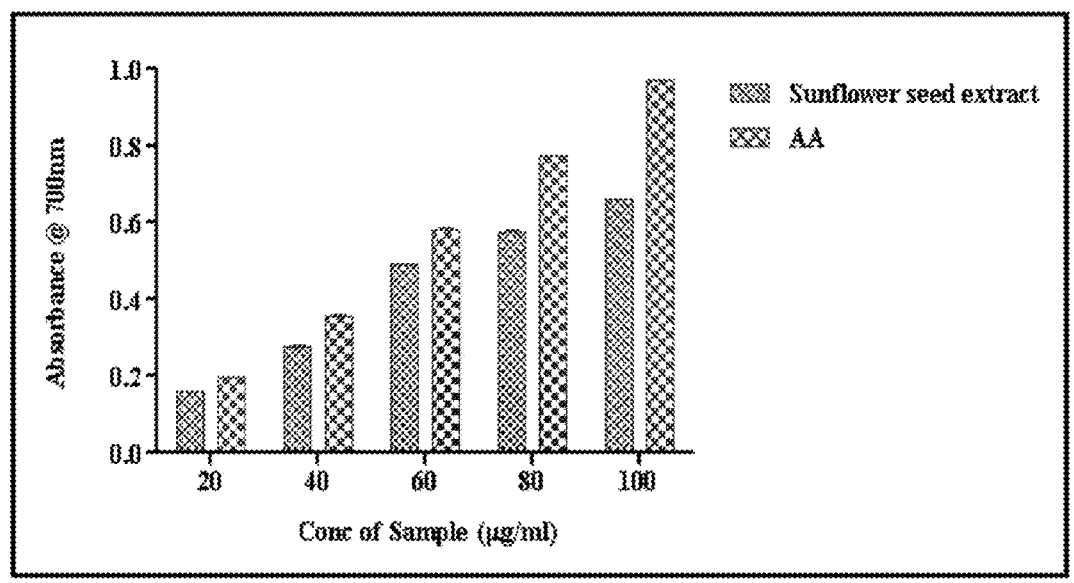
FIG. 8 shows reducing power activity of a composition according to the invention.

The superoxide radicals can be measured by its ability to reduce NBT. The ability of the composition and the reference compound ascorbic acid to quench superoxide radicals from reaction mixture was reflected in the decrease of the absorbance a 560 nm. From the results (FIG. 8 & Table 6), it can be put forward that the composition is a potent scavenger of superoxide radical.

TABLE 6

SUPEROXIDE SCAVENGING ACTIVITY

| | Composition | | Ascorbic acid | |
|---|---|---|---|---|
| Conc in µg/ml | Absorbance @560 nm | % inhibition | Absorbance @560 nm | % inhibition |
| Blank | 0.194 | | 0.250 | |
| 20 | 0.165 | 14.95 | 0.038 | 84.80 |
| 40 | 0.097 | 50.00 | 0.037 | 85.20 |
| 60 | 0.064 | 67.01 | 0.029 | 88.40 |
| 80 | 0.050 | 74.23 | 0.027 | 89.20 |
| 100 | 0.038 | 80.41 | 0.026 | 89.60 |

4.3. Reducing Power Assay

The reductive ability of the samples was determined by Oyaizu, 1986. The test samples were mixed with 2.5 ml of 0.2 M phosphate buffer (pH 6.6) and 2.5 ml of 1% potassium ferricyanide [$K_3Fe(CN)_6$]. Reaction mixture was incubated at 50° C. for 20 min, added 2.5 ml of 10% trichloroacetic acid, then centrifuged (650 rpm at room temperature) for 10 min. The upper layer solution (2.5 ml) was mixed with 2.5 ml of distilled water and 0.5 ml of 0.1% $FeCl_3$. Absorbance was measured at 700 nm. Higher absorbance at 700 nm indicates higher reducing power ability.

Result

Figure 9:
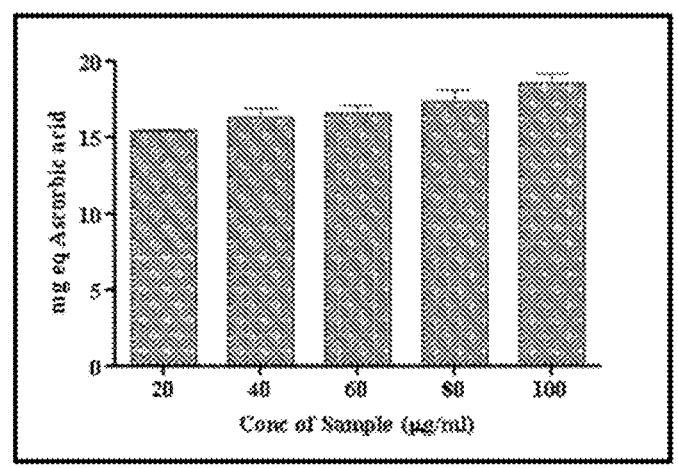
FIG. 9 shows total antioxidant capacity of a composition according to the invention.

As illustrated in FIG. 4, $Fe^{3+}$ to $Fe^{2+}$ transformation in the presence of the composition and reference compound ascorbic acid was performed to measure the reductive capability. Throughout the concentration range (20-100 µg/ml), the composition and the standard showed nearly the same trend in their reductive capability, although all the composition exhibited a lower activity than the standard. At a concentration of 100 µg/ml, absorbance of the composition and ascorbic acid was found to be 0.660 and 0.970 respectively (Table 7 FIG. 9).

TABLE 7

REDUCING POWER ACTIVITY

| | Composition | Ascorbic acid |
|---|---|---|
| 20 | 0.087 | 15.46 |
| 40 | 0.098 | 16.60 |
| 60 | 0.102 | 16.61 |
| 80 | 0.111 | 17.33 |
| 100 | 0.127 | 18.59 |

4.4. Total Antioxidant Activity

The phosphomolybdenum method is based on the reduction of Mo (VI) to Mo (V) by the antioxidant compound and the formation of a green phosphate/Mo (V) complex with a maximal absorption at 695 nm. The antioxidant activity of the test sample was determined by the phosphomolybdenum method as described by Prieto et al. 1999. Briefly, 0.3 ml of test sample combined with 3 ml of reagent solution (0.6 M sulfuric acid, 28 mM sodium phosphate and 4 mM ammonium molybdate). The reaction mixture was incubated at 95° C. for 90 min and cooled to room temperature. Measured the absorbance of the solution at 695 nm against blank. The total antioxidant capacity is expressed as the number of equivalents of ascorbic acid (AAE).

Results

Figure 10:
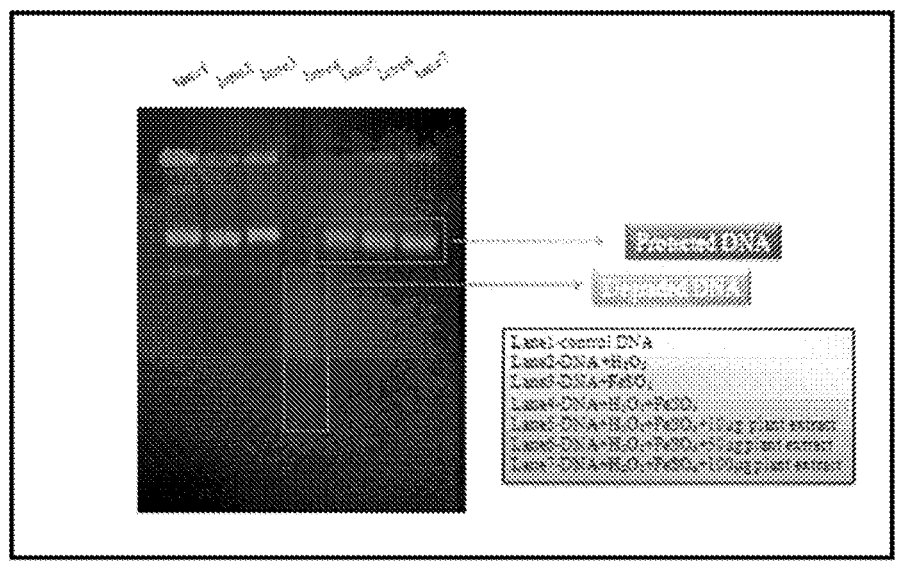
FIG. 10 shows the protective role of a composition according to the invention against oxidative DNA damage.

Total antioxidant capacity of the composition, expressed as the number gram equivalents ascorbic acid, is shown in Table 8. FIG. 10 shows the reductive capabilities of the composition and it was found remarkable. The reducing power of the composition was observed to rise in a dose-dependent manner.

TABLE 8

DETERMINATION OF TOTAL ANTIOXIDANT ACTIVITY PROTECTIVE EFFECT ON DNA SCISSION-INDUCED BY HYDROXYL RADICAL

| | Composition | |
|---|---|---|
| Conc in µg/ml | Absorbance @695 nm | AAE |
| 20 | 0.087 | 15.46 |
| 40 | 0.098 | 16.60 |
| 60 | 0.102 | 16.61 |
| 80 | 0.111 | 17.33 |
| 100 | 0.127 | 18.59 |

Despite concerns regarding the specificity and validity of the TBA assay, viz. possible interference with haemoglobin or biliverdin present in the sample, potential thermal degradation due to heating during the assay, presence of iron in the assay reagents, rapid metabolism of MDA, and low representativeness of MDA among lipid peroxides (less than 1%), the assay is still chosen by several researchers and is thus useful for comparative purposes. Furthermore, OH. radicals can also enhance DNA damage, via attack on its phosphate bonds; this type of degradation results in smaller fragments, which can be separated by agarose electrophoresis.

In this assay hydroxyl radicals are typically generated within a mixture of ascorbic acid, $H_2O_2$ and Fe3+-ethylenediaminetetracetic acid (EDTA); those radicals that are not scavenged by other components of the reaction mixture will eventually attack deoxyribose, thus degrading it into a series of fragments. Some of the fragments (or even all of them) react upon heating with thiobarbituric acid (TBA), at low pH, thus yielding a pink chromogen: this TBA adduct possesses a three-carbon dialdehyde, malondialdehyde (MDA). If an OH scavenger is meanwhile added to the reaction mixture, it will compete with deoxyribose for OH radicals, and consequently inhibit deoxyribose degradation.

Reaction Mixture: (Xican Li et.al)

The experiment was conducted using calf thymus DNA. Briefly, sample was dissolved in ethanol at 1 mg/mL. 50 µl of different concentration of sample was then separately taken into mini tubes followed by addition of 400 µL of phosphate buffer (0.2 mol/L, pH 7.4). Subsequently, 50 µL DNA sodium, 50 µL $H_2O_2$, 50 µL $FeCl_3$ and 50 µL $Na_2EDTA$ (1 mmol/L) were added. The reaction was initiated by adding 50 µL ascorbic acid (18 mmol/L) and the total volume of the reaction mixture was adjusted to 800 µL with buffer. After incubation in a water bath at 55° C. for 20 min, the reaction was terminated by adding 250 µL TCA.

The color was then developed by addition of 150 µL of TBA and heating in an oven at 105° C. for 15 min. The mixture was cooled and absorbance was measured at 532 nm against the buffer (as blank). The percent of protection against DNA damage is expressed Protective effect %=$(1-A/A_0) \times 100$ Where $A_0$ is the absorbance of the mixture without sample, and A is the absorbance of the mixture with sample.

Results

Figure 11:
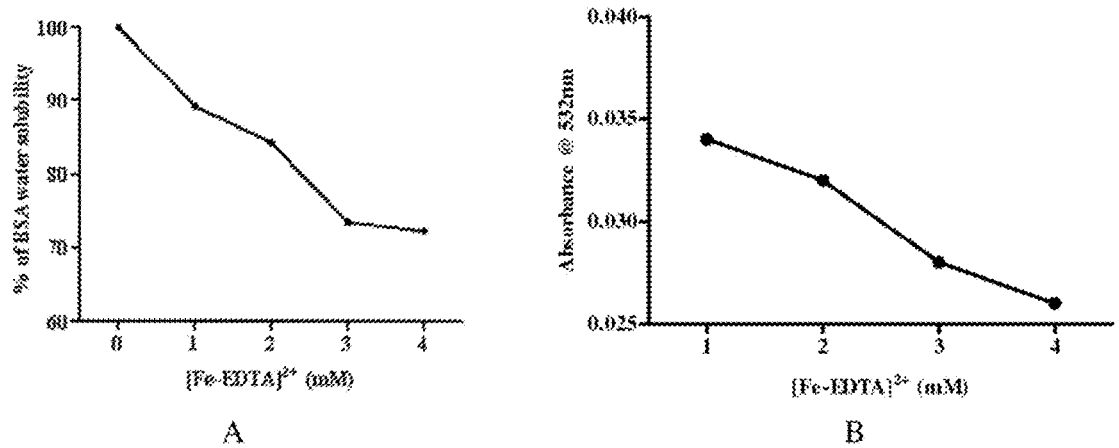
FIG. 11 shows, for a composition of the invention, (A) insolubilization of BSA exposed to Fenton's reaction system, and (B) determination of OH⁻ radical at different concentrations of chelated iron (Fenton's reaction system).

It is well known that hydroxyl radical (OH) is generated in human body via Fenton reaction. Since OH radical has extreme reactivity, it can easily damage DNA to produce malondialdehyde (MDA) and various oxidative lesions. MDA combines TBA (2-thiobarbituric acid) to produce TBARS (thiobarbituric acid reactive substances) which resent a maximum absorbance at 530 nm. On the other hand, as the oxidative lesions have no conjugative system in the molecules, they cannot be detected by a spectrophotometer at 530 nm. It means that these oxidative lesions can bring about no interference with the determination of MDA. Hence, the value of $A_{532}$ can evaluate the amount of MDA, and ultimately reflect the extent of DNA damage. Based on the formula "protective effect", it can be deduced that the decrease of $A_{532}$ value indicates a protective effect against DNA damage. As seen in above graph when compared to Standard BHA, the composition dose dependently increased the protective effect against DNA damage from 10-100 µg/mL. At 100 µg concentration the percentage protective effect of the composition and BHA was found to be 91.82% and 51.37% respectively. (Table 9, FIG. 11).

TABLE 9

DNA protectivity by using BHA as a Standard

| Concentration in | % protective effect | |
| --- | --- | --- |
| µg/ml | BHA | Composition |
| 10 | 15.79 ± 0.89 | 87.03 ± 0.19 |
| 20 | 19.25 ± 1.09 | 87.80 ± 0.63 |
| 40 | 32.50 ± 2.12 | 89.03 ± 1.41 |
| 60 | 39.16 ± 0.33 | 90.54 ± 0.79 |
| 80 | 43.04 ± 0.29 | 91.41 ± 0.74 |
| 100 | 51.37 ± 4.06 | 91.82 ± 0.41 |

4.5. Protective Role Against Oxidative DNA Damage

This assay was based on the ability of the composition of Example 1 to protect the plasmid DNA pBR322 against damage caused by hydroxyl (OH) radicals. Hydroxyl radicals generated by the Fenton reaction are known to cause oxidatively induced breaks in DNA strands, resulting in decreased super coiled form and conversion to its open circular forms. Exposure of plasmid DNA to Fenton's reagent ultimately results in strand breaks, mainly due to the generation of reactive species-hydroxyl radical and the subsequent free radical-induced reaction on plasmid DNA. Hydroxyl radicals react with nitrogenous bases of DNA producing base radicals and sugar radicals. The base radicals in turn react with the sugar moiety causing breakage of sugar phosphate backbone of nucleic acid, resulting in strand break.

Plasmid DNA (pBR322) with a concentration of 0.5 µg/3 µl was treated with Fenton's reagent (30% $H_2O_2$+2 mM $FeSO_4$) and different concentrations of composition (10 µg, 50 µg and 100 µg) incubated for 1 hour at 37° C. At the same control DNA, DNA treated with 2 mM $FeSO_4$, DNA treated with 30% $H_2O_2$, DNA treated with 2 mM $FeSO_4$ and 30% $H_2O_2$) were run simultaneously. Each mixture was incubated at 37° C. for one hour. After incubation, 3 µl (6× loading dye) was added to each reaction mixture, the samples were loaded on a 1% agarose gel and visualized with UV illuminator.

Result

Figure 12:
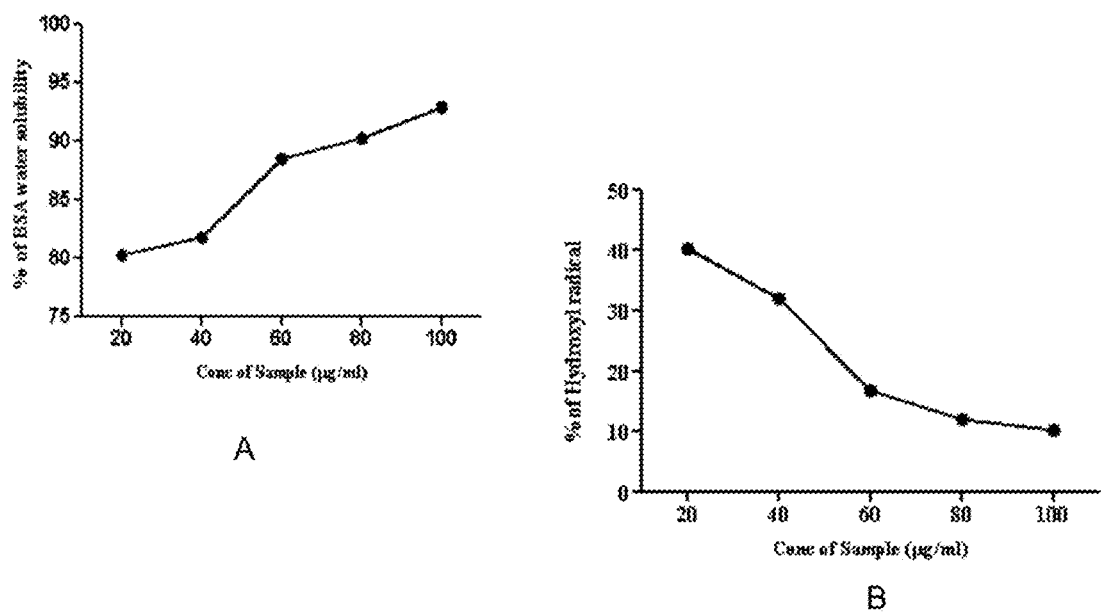
FIG. 12 shows the effect of a composition according to the invention on (A) the solubility of BSA exposed to Fenton's reaction system (3 mM chelated iron concentration), and (B) hydroxyl radical scavenging.

The DNA damage study is a reliable assay to evaluate the protective role of an agent against ROS mediated oxidative stress. Protection of vital biological macromolecules such as nucleic acids is the major mechanism by which the drugs do exert their antioxidant property. In the present study, the composition showed DNA protection against damage induced by Fenton's reagent. The composition at concentrations of 50 and 100 µg was highly effective in retaining the structural integrity of plasmid DNA as evident in FIG. 12.

4.6 Protective Role Against the Hydroxyl Radical Mediated Cross-Linking of Proteins In Vitro In the last decades there has been an increasing interest in the role that reactive oxygen species (ROS) and antioxidants may play in the ageing process and in the development of diseases associated with old age. Increased amount of oxidized proteins have been experimentally demonstrated in the ageing human brain and many rodent tissues (Floyd et al., 2001). There are evidences for the increase in the rate of ROS production and subsequent rate of ROS mediated protein damage with age. The involvement of oxidative damage in aging has prompted studies to examine the expected beneficial effects of antioxidant supplementation.

We considered worthwhile to study the antioxidant properties of the composition in a non-lipid environment of a pure protein. Hence, we adopted the method of Zs.-Nagy and Nagy, 1980 for recording changes in water solubility of the model protein bovine serum albumin (BSA) exposed to free radicals generated by an inorganic chemical system. In the present study we used the Fenton reaction system of $Fe^{2+}/EDTA/H_2O_2$ as a source of free radicals to prove the composition to protect BSA against free radical mediated cross-linking.

Protein Cross-Linking

Bovine serum albumin (BSA), a completely water-soluble protein, was polymerized by hydroxyl radicals generated by the Fenton reaction system of $Fe^{2+}/EDTA/H_2O_2$. As a result the protein loses its water solubility and the polymerized product precipitates. The decrease in the concentration of the water soluble protein can be easily detected.

The in vitro incubation mixtures contained reagents, added in the sequence as follows, at the final concentrations: BSA (0.8 mg/ml), phosphate buffer, pH 7.4 (10 mM), water to reach 2.5 ml total volume, various concentrations of the composition, EDTA (0-4.8 mM), $FeSO_4$ (0-4 mM) and $H_2O_2$ (0.2%). To chelate iron completely 1.2 molar excess of EDTA was always used. The reaction mixture was incubated for 20 min at ambient temperature then centrifuged at 3500 rpm for 10 min. The supernatant was precipitated with an equal volume of trichloroacetic acid (10%) at 0° C. followed by centrifugation at 3500 rpm for 10 min. The precipitate thus obtained was redissolved in 1 ml of $Na_2CO_3$ (10%) in NaOH (0.5 M) and the final volume made upto 2.5 ml by water. An aliquot of the solution was used for protein determination using Bradford reagent (Sigma). The yield of OH radicals generated in the incubations was determined on the basis of degradation of deoxyribose as described by Halliwell et al., 1987.

SDS-PAGE Electrophoresis

The 0.5 mg protein pellets isolated from the incubation mixtures of BSA with the Fenton system as described above, in the presence of 4 mM ferrous sulphate, were treated with 5% SDS either in the presence or absence of 5% 2-mercaptoethanol. Electrophoresis was conducted with stacking and separating gels containing 4 and 7.5% acrylamide, respectively. The gels were stained in 0.2% coomassie blue, and destained in 10% acetic acid in 25% methanol.

Result

Figure 13:
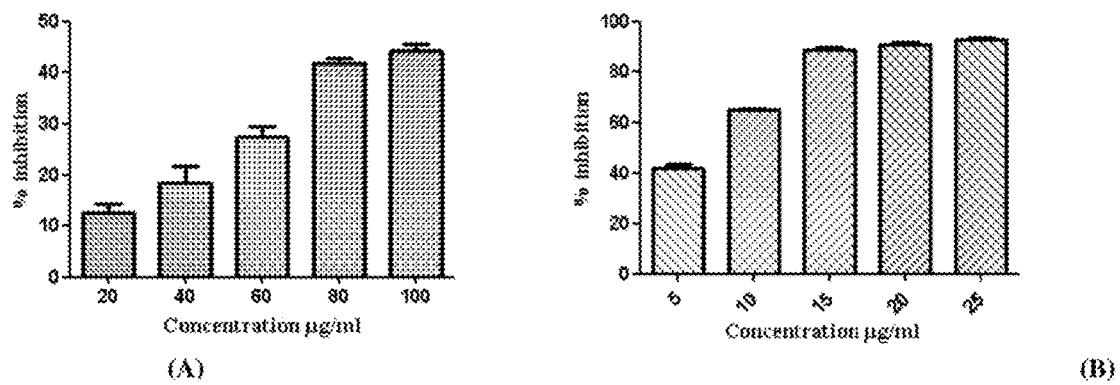
FIG. 13 shows comparative inhibition of pancreatic lipase activity by (A) a composition according to the invention, and (B) Orlistat.

In the present work we have recorded the changes in water solubility of BSA exposed to chemical source of hydroxyl free radicals to characterize the anti-oxidant efficiency of the composition of Example 1 in a non-lipid protein system. We used the Fenton reaction system which gave a defined flow of hydroxyl radicals. We used deoxyribose as a detection molecule to determine the yield of hydroxyl radicals in the Fenton's reaction system. BSA, a completely water-soluble protein, exposed to the above Fenton's reaction system, was losing its water solubility depending on the concentration of the chelated iron, as shown in FIG. 13A. The initial insolubilization was noticed at 1 mM iron and slow up to 2 mM followed by an exponential decrease in % solubility of BSA at higher concentrations. The OH. radical decreased with increased concentration of chelated iron (1-4 mM) as the radicals were used up to polymerize BSA (FIG. 13B).

Figure 14:
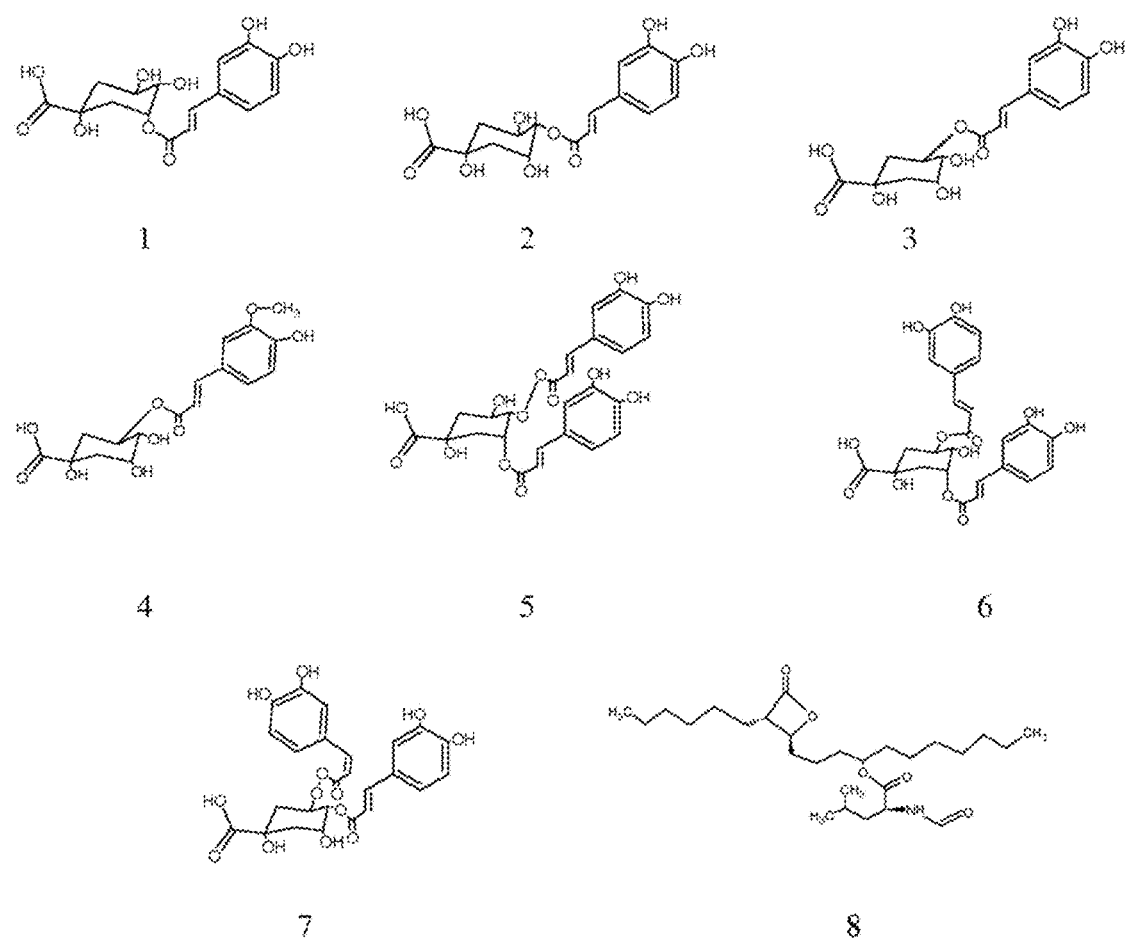
FIG. 14 shows the structure of ligand molecules (1) 3-O-Caffeoylquinic acid, (2) 4-O- Caffeoylquinic acid, (3) 5-O- Caffeoylquinic acid, (4) 5-O-Feruloylquinic acid, (5) 3,4-O-Dicaffeoylquinic acid, (6) 3,5-O-Dicaffeoylquinic acid, (7) 4,5-O-Dicaffeoylquinic acid, and (8) Orlistat.

The composition was added to the BSA incubations and inhibited protein cross-linking in a concentration-dependent way as shown in FIG. 14A. Similarly, the composition of Example 1 was effective in scavenging the OH. radicals generated by the Fenton's reaction system (FIG. 14B). There was a significant correlation observed between the BSA solubility and the OH. radicals indicating a critical role of free radicals in BSA cross-linking under the conditions employed in this study.

The results obtained in this study strongly indicated that the insolubilization of BSA induced by the Fenton's system of $Fe^{2+}/EDTA/H_2O_2$ was caused by free OH radical mediated polymerization giving rise to true covalent cross-links. The model system was found suitable for convenient testing of OH. radical scavenging and hence the protective role of the composition in a non-lipid environment.

Example 5—Effect of Composition in Obesity Management 5.1 In Vitro Anti-Lipase Activity In order to provide the scientific evidence for the effectiveness of the composition of Example 1 in managing obesity, we have performed the in vitro anti-lipase assay using the porcine pancreatic lipase activity as a measure.

Substrate: 10 mM p-NPB (p-nitrophenylbutyrate)

Enzyme: Porcine pancreatic lipase

The ability of the composition to inhibit pancreatic lipase was measured using the method previously reported by Kim et al., 2012. Briefly, an enzyme buffer was prepared by the addition of 6 μL porcine pancreatic lipase solution (Sigma-Aldrich) in buffer containing 10 mM MOPS (morpholinepropanesulphonic acid) and 1 mM EDTA, pH 6.8, to 169 μL Tris buffer (100 mM Tris-HCl and 5 mM $CaCl_2$, pH 7.0). Then, 20 μL of the composition at the test concentration (20-100 μg/mL) was mixed with 175 μL enzyme buffer and incubated for 15 min at 37° C. with 5 μL substrate solution (10 mM p-NPB (p-nitrophenylbutyrate) in dimethyl formamide); the enzymatic reactions were allowed to proceed for 15 min at 37° C. Lipase activity was determined by measuring the hydrolysis of p-NPB top-nitro phenol at 405 nm using UV spectrophotometer. Inhibition of lipase activity was expressed as the percentage decrease in OD when porcine pancreatic lipase was incubated with the test materials. Lipase inhibition (%) was calculated according the following Formula:

Inhibition %=100−{$B-b/A-a$×100} where 'A' is the activity without inhibitor, 'a' is the negative control without inhibitor, 'B' is the activity with inhibitor, and 'b' is the negative control with inhibitor.

Figure 15:
FIG. 15 shows the 3D structure of pancreatic lipase.

The results were expressed as an average. Inhibition of pancreatic lipase is expressed in terms of percentage. The composition exhibited an inhibitory effect on lipase with a maximum percentage inhibition of 44.08% at a concentration of 100 μg/mL. The results though were comparable to standard drug Orlistat, the composition was not more effective than the positive control (FIG. 15). However, Orlistat has been associated with side effects such as gas with oily spotting, stomach pain, irregular menstrual periods, and headaches.

Result

The results of anti-lipase activity were expressed as the percentage inhibition of pancreatic lipase and the composition had shown appreciable inhibitory spectrum at various concentrations tested. There was a moderate decrease in the enzyme activity as evident by the gradual increase in percentage inhibition following incubation with the composition. The results were comparable to standard drug Orlistat (FIG. 15).

5.2 In Silico Docking Studies with Human Pancreatic Lipase

In the present study, in order to evaluate the comparative inhibition of pancreatic lipase by the standard drug Orlistat and the composition, we have performed the in silico docking analysis.

Figure 16:
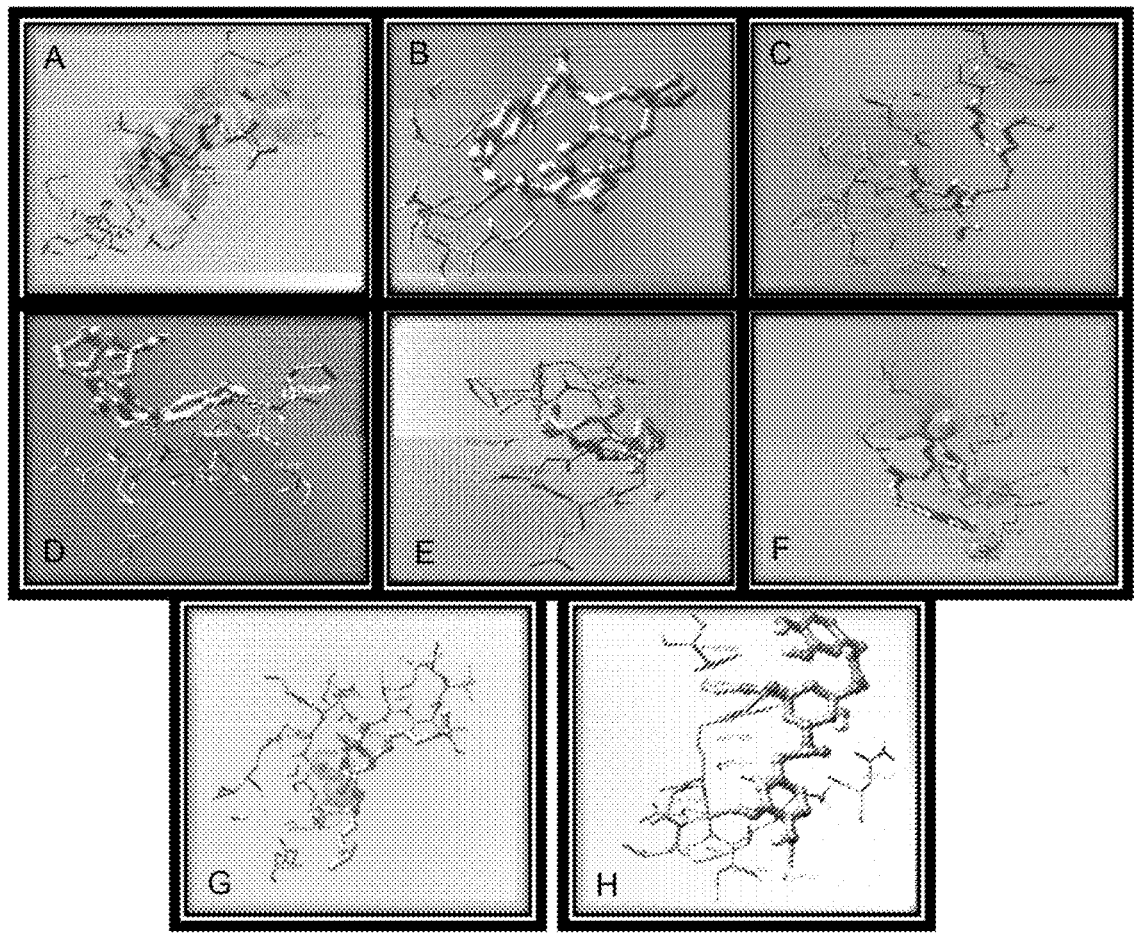
FIG. 16 shows the orientation of ligands in the active pocket of pancreatic lipase for (A) 3-O-Caffeoylquinic acid, (B) 4-O- Caffeoylquinic acid, (C) 5-O- Caffeoylquinic acid, (D) 5-O-Feruloylquinic acid, (E) 3,4-O-Dicaffeoylquinic acid, (F) 3,5-O-Dicaffeoylquinic acid, (G) 4,5-O-Dicaffeoylquinic acid, and (H) Orlistat.

AutoDock tools was utilized to generate grids, calculate dock score and evaluate the conformers of inhibitors bound in the active site of pancreatic lipase as targets for anti-obesity activity. Automated docking is a graphical user interface. AutoDock 4.2 was employed to get docking and binding scores; which is implemented by Lamarckian genetic algorithm method. The ligand molecules i.e., the isomers of chlorogenic acid (FIG. 16) and Orlistat were designed and the structure was analyzed using ACD/Chemsketch. The PRODRG server was used to minimise energy of drug compounds and 3D coordinates were prepared. The protein structure file (PDB ID: 1LPB) (FIG. 17) was taken from PDB and was edited by removing the hetero atoms using Python molecule viewer. The grid map was centred at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Result

The isomers of chlorogenic acid in the composition exhibited pronounced lipase inhibition activity as evident from the thermodynamic parameters studied (Table 10). The interaction of isomers with active pocket residues was firm as it required lesser energy as compared to the standard drug Orlistat (FIG. 18). The study supports the claim for the anti-obesity effects of the composition as evident from the strong inhibition of pancreatic lipase by the isomers of chlorogenic acid.

TABLE 10

MOLECULAR DOCKING RESULTS OF PANCREATIC LIPASE

| Molecule | Binding energy (kJmol$^{-1}$) | Ligand efficiency (kJ/mol$^{-1}$) | Inhibitory constant | H-bonds | Interactions |
|---|---|---|---|---|---|
| 3-O-Caffeoylquinic acid | −4.64 | −0.19 | 399.38 | 4 | Lys238, Asn10 |
| 4-O-Caffeoylquinic acid | −3.69 | −0.15 | 1.96 | 5 | Glu385, Ile371, Lys373, Glu370 |
| 5-O-Caffeoylquinic acid | −3.22 | −0.13 | 4.37 | 5 | Ile9, Lys39 |
| 5-O-Feruloylquinic acid | −3.39 | −0.13 | 3.25 | 4 | Ile371, Lys373 |
| 3,4-O-Dicaffeoylquinic acid | −1.3 | −0.04 | 111.7 | 6 | Asn406, Lys373, His354, Asn406 |
| 3,5-O-Dicaffeoylquinic acid | −2.58 | −0.07 | 12.9 | 4 | Glu15, Ile9, Asn240 |
| 4,5-O-Dicaffeoylquinic acid | −2.06 | −0.06 | 31.13 | 4 | Arg65, Glu64 |
| Orlistat (Std) | −1.03 | −0.03 | 176.96 | 2 | Lys238 |

CONCLUSION

The increased levels of systemic oxidative stress that occur in obesity may contribute to the obesity-associated development of secondary complications. Medicinal herbs have drawn attention during recent past in the obesity management mediated through various mechanisms including oxidative stress. Plants are a rich source of polyphenols, major group of biologically active secondary metabolites. These factors attribute mainly to the therapeutic benefits of plants including antioxidant activity. This scientific report is based on a comprehensive study in vitro and in silico analysis to validate the health benefits of the composition of Example 1 in obesity management.

Studies have suggested that excessive intake of calories are related to chronic diseases which includes obesity. These are all linked to oxidative stress, causing an imbalance of pro oxidants and antioxidants in cellular systems, which impairs normal biological functions (Droge, 2002).

REFERENCES

1. Ado M. A., Abas F., Mohammed A. S., Ghazali H. M. (2013) Anti- and Pro-Lipase Activity of Selected Medicinal, Herbal and Aquatic Plants, and Structure Elucidation of an Anti-Lipase Compound. Molecules, 18, 14651-14669.
2. Agribusiness Handbook (2010) Sunflower crude and refined oils. FAO (Food and Agriculture Organization of the United Nations) Investment Centre Division, in collaboration with FAO's Rural Infrastructure and Agro-Industries Division, 1-41.
3. Borenfreund, E., Puemer, JA (1990) Tissue Cult. Meth. 9: 7-0 (1984).
4. Braca A, de Tommasi N, di Bari L, Pizza C, Politi M, Morelli I (2001). Antioxidant principles from Bauhinia terapotensis. J Nat Prod., 64, 892-895.
5. Droge, W., (2002) Free radicals in the physiological control of cell function. Physiol. Rev., 82: 47-95.
6. Floyd R A, West M, Hensley K (2001). Oxidative biochemical markers; clues to understanding ageing in long-lived species. Exp Gerontol., 36, 619-640
7. Formica J V, Regelson W (1995). Food Chem Toxicol., 33, 1061.
8. G. Nagaraj (1995) Quality and utility of oilseeds Directorate Of Oilseeds Research (Indian Council of Agricultural Research), Hyderabad.
9. Gayathri Gunalan, Neelima Myla, Balabhaskar R (2012). In vitro antioxidant analysis of selected coffee bean varieties. J chem pharm res., 4(4), 2126-2132
10. Halliwell B, Gutteridge J M, Aruoma O I (1987). The deoxyribose method: a simple 'test tube' assay for determination of rate constants for reactions of hydroxyl radicals. Anal Biochem., 165, 215-219
11. Jung T, Holm A, Catalgol B, Grune T (2009). Age-related differences in oxidative protein-damage in young and senescent fibroblasts. Arch Biochem Biophysics, 483, 127-135
12. Maron D M, Ames B N (1983). Revised methods for the Salmonella mutagenicity test. Mutat Res., 113, 173-215.
13. Nishikimi M, Rao N A, Yagi K (1972). The occurrence of superoxide anion in the reaction of reduced phenazine methosulfate and molecular oxygen. Biochem Biophys Res Commun., 46, 849-854
14. Oyazu M (1986). Studies of product browning reaction: antioxidant activity of producbrowning reaction from glucosamine. Jap J Nut., 44, 397-315
15. Packer L, Cadenas E, Davies K J A (2008). Free radicals and exercise: An introduction. Free Radical Biol Med., 44, 123-125.
16. Pedrosa, M. M., Muzquiz, M., Garcia-Vallejo, C., Burbano, C., Cuadrado, C., Ayet, G. and Robredo, L. M., 2000. Determination of caffeic and chlorogenic acids and their derivatives in different sunflower seeds. J. Sci. Food Agric. 80: 459-464.
17. Preedy V. R, Watson R. R., Patel V. B. (2011) Nuts and seeds in health and disease prevention, Elsevier, 1098-1105, ISBN 978-0-12-375688-6.
18. Priteo O, Pineda M, Aguilar M (1999). Spectrophotometric quantitation of antioxidant capacity through the formation of phosphomolybdenum complex: specific application to the determination of vitamin E. Anal Biochem., 269, 337-341
19. Rodriguez A, Infante D (2011). Characterization in silico of flavonoids biosynthesis in Theobroma cacao L. Net Biol., 1, 34-45.
20. Shengxi Meng, 1 Jianmei Cao, 1,2 Qin Feng, 1 Jinghua Peng, 1 and Yiyang Hu1,3(2013) Roles of Chlorogenic Acid on Regulating Glucose and Lipids Metabolism: A Review Evidence-Based Complementary and Alternative Medicine Volume 2013, Article ID 801457, 11 pages
21. So F V, Guthrie N, Chambers A F, Moussa M, Carroll K K (1996). Nutr Cancer., 26, 167
22. Vogel H J, Bonner D M (1956). Acetylornithinase of E. coli: partial purification and some properties. J Biol Chem., 218, 97-106.
23. Wells P G, McCallum G P, Chen C S, Henderson J T, Lee C J, Perstin J, Preston T J, Wiley MJ, Wong A W (2009). Oxidative stress in developmental origins of disease:

Teratogenesis, neurodevelopmental deficits, and cancer. Toxicological Sciences., 108, 4-18

24. Young Sook Kim, Youngseop Lee, Junghyun Kim, Eunjin Sohn, Chan Sik Kim, Yun Mi Lee, Kyuhyung Jo, Sodam Shin, Yoojin Song, Joo Hwan Kim, Jin Sook Kim (2012). Inhibitory activities of Cudrania *tricuspidata* leaves on pancreatic lipase in vitro and lipolysis in vivo. Evidence-Based Compl Alt Med.

25. Zs.-Nagy I, Nagy K (1980). On the role of cross-linking of cellular proteins in aging. Mech Ageing Dev., 14, 245-251.

The invention claimed is:

1. A method of modulating body weight, comprising administering to a subject in need thereof a composition comprising a sunflower seed extract that includes a mixture of chlorogenic acids having (i) 4.1+1.42% w/w 3-caffeoylquinic acid (3-CQA), (ii) 28+4.65% w/w 5-CQA, (iii) 6.5+2.25% w/w 4-CQA, (iv) 0.84+0.26% w/w 3,4-dicaffeoylquinic acid (3,4-diCQA), (v) 1.23+0.34% w/w 3,5-diCQA, and (vi) 1.85+0.42% w/w 4,5-diCQA, wherein administering the composition to the subject modulates body weight in the subject.

2. The method of claim 1, wherein the composition inhibits pancreatic lipase activity in the subject.

3. The method of claim 1, wherein administering the composition prevents or inhibits weight gain in the subject.

4. The method of claim 1, wherein administering the composition reduces body weight in the subject.

5. The method of claim 1, wherein the subject is obese.

6. The method of claim 1, wherein the subject is overweight.

7. The method of claim 1, wherein the composition is administered orally, buccally, sub-lingually, parenterally, intravenously, intravaginally, rectally, or by inhalation.

8. The method of claim 1, wherein the composition is in the form of a powder, liquid, pill, tablet, pellet, capsule, thin film, solution, spray, syrup, linctus, lozenge, pastille, chewing gum, paste, suspension, emulsion, gel, drop, buccal patch, bead, gummy, gel, or sol.

9. The method of claim 1, wherein the sunflower seed extract has a total chlorogenic acid content of 42.50 +/−2.5 w/w %.

10. The method of claim 1, wherein the sunflower seed extract has an antioxidant scavenging activity of about 87.88% at a concentration of 100 µg/ml in vitro.

11. The method of claim 1, wherein the sunflower seed extract is obtained by extracting sunflower seeds in a solvent consisting of water.

* * * * *